United States Patent [19]

Zoche et al.

[11] Patent Number: 4,560,787

[45] Date of Patent: Dec. 24, 1985

[54] PROCESS FOR PREPARING 10,11-DIHYDRO-5H-DIBENZO[a,d]CYCLOHEPTENE-5-ONE COMPOUNDS

[75] Inventors: Günter Zoche, Bonn; Wilhelm Vogt, Cologne, both of Fed. Rep. of Germany

[73] Assignee: Dynamit Nobel AG, Troisdorf, Fed. Rep. of Germany

[21] Appl. No.: 632,672

[22] Filed: Jul. 19, 1984

Related U.S. Application Data

[63] Continuation of Ser. No. 422,785, Sep. 24, 1982, abandoned.

[30] Foreign Application Priority Data

Sep. 30, 1981 [DE]  Fed. Rep. of Germany ....... 3138842
Oct. 31, 1981 [DE]  Fed. Rep. of Germany ....... 3143307

[51] Int. Cl.$^4$ ............................................. C07C 45/45
[52] U.S. Cl. ....................................... 560/52; 560/80; 568/319
[58] Field of Search .................... 568/319; 560/52, 80; 260/544 D, 544 B

[56] References Cited

U.S. PATENT DOCUMENTS

| | | | |
|---|---|---|---|
| 1,963,749 | 6/1934 | Kyrides | 260/544 D |
| 3,052,721 | 9/1962 | Bernstein et al. | 568/319 |
| 3,287,409 | 11/1966 | Leonard et al. | 568/319 |
| 3,344,185 | 9/1967 | Leonard | 424/324 |
| 3,350,405 | 10/1967 | Schulenberg et al. | 568/319 |
| 3,369,044 | 2/1968 | Leonard et al. | 260/544 B |
| 3,409,640 | 11/1968 | Villani | 568/319 |
| 3,459,859 | 8/1969 | Leonard | 424/324 |
| 3,502,697 | 3/1970 | Woodward | 568/319 |

OTHER PUBLICATIONS

*J. Am. Chem. Soc.*, vol. 73, 1951, pp. 1668–1673.
Olah, G. (ed.), *Freidel–Crafts and Related Reactions*, vol. I, Interscience Publishers, New York, 1963, pp. 201–204.
Weygand et al., *Preparative Organic Chemistry*, John Wiley and Sons, New York, 1972, pp. 247–251.
*Chem. Ber.*, vol. 83, 1950, pp. 367–371.
*Helv. Chim. Acta*, vol. 36, 1953, pp. 1489–1499.
*J. Med. Pharm. Chem.*, vol. 4, 1961, pp. 335–349, Vander Stelt et al.

*Primary Examiner*—James H. Reamer
*Assistant Examiner*—Patricia M. Scott
*Attorney, Agent, or Firm*—Felfe & Lynch

[57] ABSTRACT

The present invention relates to a method of preparing 10,11-dihydro-5H-dibenzo[a,d]cycloheptene-5-one or substitution products thereof from dibenzyl-o-carboxylic acid or its corresponding substitution products, by cyclocondensation. The cyclocondensation is performed in either of two ways, namely (a) with catalytic amounts of a concentrated acid as catalyst, or (b) with the aid of di- and/or tri-chloromethyl aromatic compounds in the presence of catalysts, preferably catalysts from the group of the Lewis acids.

11 Claims, No Drawings

PROCESS FOR PREPARING 10,11-DIHYDRO-5H-DIBENZO[a,d]CYCLOHEPTENE-5-ONE COMPOUNDS

This application is a continuation of application Ser. No. 422,785, filed Sept. 24, 1982, abandoned.

This invention relates to a process for preparing 10,11-dihydro-5H-dibenzo[a,d]5-one compounds, especially dibenzosuberone (DBS). In the process of the invention 10,11-dihydro-5H-dibenzo[a,d]5-one and its substitution products are prepared by the cyclocondensation of dibenzyl-o-carboxylic acid or the corresponding substitution products.

DBS is the intermediate of a series of pharmaceutical products, mainly antidepressants. Accordingly, the substituents in the drugs determine the nature and amount of the substituents in the starting substance and in the product.

The lowest-cost method for the synthesis of DBS operates through dibenzyl-o-carboxylic acid (I). The cyclization of dibenzyl-o-carboxylic acid to DBS can be performed either (a) through preparation of the acid chloride (II) followed by a Friedel-Crafts reaction (J. Med. Pharm. Chem. 4, 335–49 (1961); J.Am.Chem.Soc. 73, 1668–73 (1951); Chem. Ber. 83, (1950) 367–71), or by a direct method (b) using polyphosphoric acid (PPA).

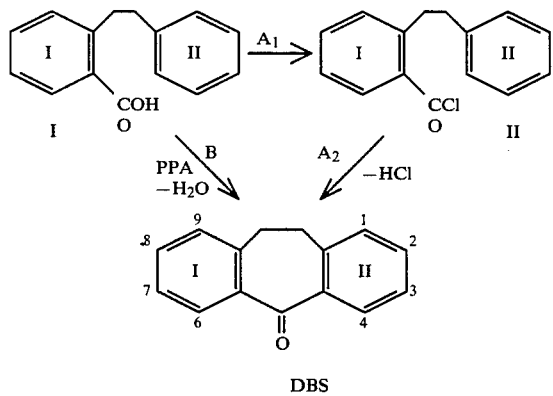

DBS

In method a, compound II can be prepared from I by the conventional methods ($SOCl_2$, $PCl_3$ etc.). In the second step, DBS is produced from II with the aid of usually large amounts of Friedel-Crafts catalysts.

Synthesis b is a one-step synthesis, but it has the disadvantage that large amounts of PPA are needed, namely 2 to 50 times the weight of compound I, so that high costs are involved in the PPA. Since dilute polyphosphoric acid cannot be economically transformed to PPA, the waste water is considerably contaminated.

| Literature citations | g of PPA per mole of dibenzyl-o-carboxylic acid | Reaction temp. °C. | time h | DBS yield % |
|---|---|---|---|---|
| a 1, 2, 3, 4 | 10,000 | 100 | 2 | 84 |
| b 5 | X | 170 | 2.5 | 75 |
| c 6, 7 | 1,565 | 170 | 3 | 91 |
| d 8 | 350 | 120 | 2 | 97 |

X = Information not available

Literature:
1 U.S. Pat. No. 3,344,185
2 U.S. Pat. No. 3,459,859
3 U.S. Pat. No. 3,287,409
4 U.S. Pat. No. 3,369,044
5 U.S. Pat. No. 3,052,721
6 Galenica Acta 15 (2), 77–87 (1962)
7 Helv. Chim. Acta 36, 1489–99 (1953)
8 Synthesis (1972) 612–4

Disadvantages in method b and in method a are especially the necessity of treatment with water to remove the Friedel-Crafts catalyst and the PPA and to permit isolation of the DBS, as well as the need to use one or more organic solvents.

The problem thus existed of finding a simple and economical method of cyclizing dibenzyl-o-carboxylic acid and its substitution products to obtain DBS and its substitution products.

THE INVENTION

The subject matter of the invention is a method of preparing 10,11-dihydro-5H-dibenzo[a,d]cycloheptene-5-one and its substitution products, of the formula:

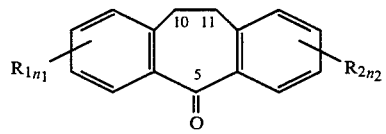

wherein hydrogen can be substituted partially by $R_1$ and/or $R_2$ and $R_1$ and $R_2$ represent:
halogen and/or
alkyl groups and/or
aryl groups and/or
aralkyl groups and/or
carboalkoxy groups, and
$n_1$ and $n_2$ have the numerical values 0, 1, 2, 3 or 4, by cyclocondensation of the corresponding dibenzyl-o-carboxylic acids, characterized in that (a) the dibenzyl-o-carboxylic acids are cyclized with catalytic amounts of a concentrated acid as catalyst or (b) the dibenzyl-o-carboxylic acids are cyclized in the presence of aromatics containing one or more kernel-bound di- and/or trichloromethyl groups, in the presence of a catalyst, to produce the above-named compound or its substitution products.

Concentrated acids used as catalysts in accordance with (a) are, for example, polyphosphoric acid, p-toluenesulfonic acid, concentrated sulfuric acid. The best yields are obtained with polyphosphoric acid or p-toluenesulfonic acid. p-Toluenesulfonic acid, however, decomposes and cannot be reused.

The amount of the concentrated acids can vary greatly. The time required to complete the transformation depends on the amount of catalyst. Therefore it is recommendable for reasons of economy to use not less catalyst than 1% of the weight of compound I. Although there are no limits to the amount of catalyst, the amount of 10% by weight will not be exceeded for the same considerations.

The use of adjuvants or solvents in unnecessary. The polyphosphoric acid can be reused repeatedly. The catalyst consumption is therefore very small. The problem of the removal of the catalyst or of its aqueous solution and of disposing of used catalyst is eliminated.

Procedure a must be performed at a reaction temperature of 180° to 280° C., preferably 220° to 260° C., for the achievement of a complete transformation, and the water of reaction must be continuously removed. This can be done in various ways. For example, the water can be removed by passing a gas stream over and/or through the reaction mixture, which should best be thoroughly stirred. The gas must be inert to all reactants. Examples of suitable gases are nitrogen, carbon dioxide and argon.

Another method is to remove the water continuously by vacuum distillation. A compromise must be made in selecting the vacuum. On the one hand, the pressure must be as low as possible in order to remove the water as quickly as possible from the reaction mixture. On the other hand, sublimation of compound I must be prevented. Suitable working pressures are between 10 and 100 Torr, preferably between 20 and 50 Torr.

The reaction b is performed in accordance with the following equation, in which benzotrichloride was selected as the trichloromethyl aromatic:

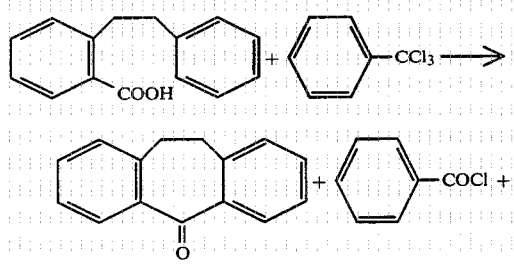

A great number of Lewis acids can be used as catalysts. Especially suitable are the iron and zinc compounds acting as Lewis acids, such as for example anhydrous iron(III) chloride, zinc chloride or iron(III) phosphate. The amount of catalyst is variable within wide limits. Amounts of as little as 0.01% of the weight of the dibenzylcarboxylic acid produces a catalytic action. However, since there is a certain interdependence between the amount of catalyst and the rate of reaction, an amount corresponding to 0.02 to 5% of the weight of the dibenzylcarboxylic acid will be used for economic reasons. However, larger amounts, up to 10% by weight, are also usable in accordance with the invention.

The reaction in accordance with b takes place at elevated temperature of 50° to 180° C., preferably 75° to 150° C. The beginning of the reaction can be detected on the basis of the evolution of HCl. In this temperature range, which generally begins at about 70° C., it is desirable first to allow the reaction to run and then, as the evolution of gas diminishes, to raise the temperature gradually to 120° to 150° C. In this temperature range the reaction is carried to the end. After the evolution of HCl ends, the dibenzosuberone can be obtained directly from the by-product acid chloride by fractional distillation. Further processing is not necessary.

It is known that trichloromethyl aromatic compounds react with carboxylic acids with the formation of the acid chlorides of carboxylic acid. It is surprising, however, that in the present case the expected acid chlorides of dibenzyl-o-carboxylic acids cyclize immediately to the corresponding dibenzosuberone with the production of hydrogen chloride. It is also surprising that this reaction is catalyzed even by the small amounts of the zinc or iron compounds, for example, referred to above.

The chloromethyl aromatics which can be used in accordance with the invention can be mononuclear or polynuclear and can have one or more di- or trichloromethyl groups. Mononuclear compounds having one or more trichloromethyl groups are used preferentially. Benzotrichloride, 1,4-bis-(trichloromethyl)benzene and 1-trichloromethyl-2-dichloromethylbenzene are given as examples. In the case of the last named compound, the dichloromethyl group also reacts in accordance with the reaction specified above. In this case the product is 3-chlorophthalide.

The chloromethyl aromatics are used preferably in a stoichiometric ratio to the dibenzylcarboxylic acid. The stoichiometry refers in this case to the number of reactive di- or trichloromethyl groups of the chloromethyl aromatic compounds. These react to form end products which also are obtained in great purity in the fractional vacuum distillation, without further purifying operations. The products thus obtained, such as benzoyl chloride, terephthalic acid dichloride or 3-chlorophthalide are also important intermediates in the chemical and pharmaceutical industry. The method of the invention accordingly has the additional advantages over the known methods that by-products are formed which are useful in the first place and in the second place do not have to be worked up by additional process steps.

Another advantage of reaction b is the high purity of the product hydrogen chloride, since low-boiling compounds, such as for example $SO_2$ or $SOCl_2$, are not present; thus the reuse of the product hydrogen chloride as synthesis gas is considerably facilitated.

Neither the reaction nor the purification or isolation of the reaction products is generally performed with the use of solvents. Thus all the extraction steps necessary for the separation of solvent, which then has to be either destoyed or processed, as in the case of the known methods, are unnecessary.

If, however, under special circumstances it is necessary to employ a solvent, this is also possible in accordance with the invention. Suitable solvents are then those which are inert under the conditions of the reaction and whose boiling temperatures are above 100° C., preferably above 150° C., such as nitrobenzene for example.

After the reaction a is completed, DBS or its substitution products are isolated from the reaction mixture by vacuum distillation. Even without the use of fractionating heads, yields of 90% and more are obtained, with respect to compound I, and purities of over 99%.

The starting substances of both procedures can have as many as 8 substituents, as many as 4 on each of the rings I and II. The substituents are preferably to be inert in the reaction, although a chemical variation of the splitting off the of the substituents is possible as long as the cyclization is not impaired.

The preferred product is dibenzosuberone, and, secondarily, substitution products having one or two substituents. Preferred substituents are methoxy, alkyl of 1 to 4 carbon atoms, and chlorine. m-Substituents in Ring II of the starting substances occur in the product in position 2.

EXAMPLES

Examples of procedure a

Example 1

A round flask of a capacity of 5 liters is charged with 1 kg of dibenzyl-o-carboxylic acid, 100 g of toluenesulfonic acid-(4)-monohydrate and a magnetic stirrer. The reaction flask is provided with a vertical glass tube 80 cm long, on the upper end of which is the vacuum connection. At a constant vacuum of 45 Torr, the flask is kept at a temperature of 240° C. by means of a metal bath, with stirring. After an hour and three quarters it is allowed to cool. The flask is changed over to simple vacuum distillation, and distillation is performed at $bp_{0.2}$ 136°–40° C. 840 g of DBS is obtained of a GC purity of 98.9%.

Example 2

Apparatus same as in Example 1. One kilogram of dibenzyl-o-carboxylic acid and 100 g of polyphosphoric acid, content 85% (alkalimetric, reckoned as $P_2O_5$; d: 2.06) are used. Cyclization is performed for 1½ hours at 240° C. and 30 to 40 Torr. After distillation 830 g of DBS is obtained with a GC purity of 99.6%.

Example 3

Apparatus same as in Example 1. One kilogram of dibenzyl-o-carboxylic acid and 10 g of polyphosphoric acid (cf. Example 2) are used. Cyclization is performed for 7 hours at 240° C. and 30 to 40 Torr. After distillation , 830 g of DBS is obtained with a GC purity of 99.1%.

Example 4

Apparatus as in Example 1, with round flask of 50 ml capacity. 10.0 g of dibenzyl-o-carboxylic acid and 0.14 g of 95% sulfuric acid are put in. Cyclization is performed for 4.5 h at 240° C. and 30 Torr. 7 g of distillate is obtained having a composition, as determined by gas chromatography, of 88.8% DBS (remainder dibenzyl-o-carboxylic acid).

Example 5

(a) The 100 ml two-necked boiling flask of a simple still serves simultaneously as the reaction vessel. It is charged with 10.0 g of dibenzyl-o-carboxylic acid and 1.0 g of polyphosphoric acid. The second neck of the flask serves for the introduction of gas. Throughout the reaction time a slow stream of nitrogen is passed over the flask contents while they are stirred with a magnetic stirrer. For this purpose the flask is kept for 3.5 h at 240° C. Then the DBS is removed by vacuum distillation. 7.5 g of DBS is obtained with a GC purity of 99.6%.

(b) An additional 10.0 g of dibenzyl-o-carboxylic acid is added to the distillation residue of Example 5a (no more catalyst is added). The process is continued as in Example 5a. In the distillation, 8.2 g of DBS is obtained with a GC purity of 99.4%.

(c) The distillation residue of Example 5b is treated again as described in Example 5b, and 9.0 g of DBS is obtained with a GC purity of 99.0%.

Example 6

Example 2 is repeated with the equivalent amount of 2-[2-(m-methoxyphenyl)-ethyl]-benzoic acid (mp 117° to 119° C.) instead of dibenzyl-o-carboxylic acid, and the product, in a corresponding yield, is 2-methoxy-10,11-dihydro-5H-dibenzo-[a,d]cycloheptene-5-one (mp 71° to 73° C. from a mixture of water and ethanol).

Examples 7 and 8

Example 2 is repeated with equivalent amounts of (a) 2-[2-p-methylphenyl)-ethyl]-benzoic acid (mp 82° C.) and (b) 2-[2-p-chlorophenyl)-ethyl]-benzoic acid (mp 122° C.), resulting in good yields of (a) 3-methyl-10,11-dihydro-5H-dibenzo[a,d]cycloheptene-5-one (mp 34° to 35° C.) and (b) 3-chloro-10,11-dihydro-5H-dibenzo[a,d]cycloheptene-5-one (mp 64° to 65° C.).

Examples of Procedure b

Example 9

In a 100 ml glass flask, 22.6 g of dibenzyl-o-carboxylic acid, 19.5 g of benzotrichloride and 1.0 g of $FeCl_3$ (anhydrous) are heated at first at 80° C. with the exclusion of moisture and with stirring. When the production of HCl that occurs at this temperature diminishes, the temperature is gradually raised to 125° C. The reaction ends after a total of 2 hours. Then the flask content is distilled in vacuo. The fraction $bp_{0.2}$: 136°–40° C. consists of 18.0 g of dibenzosuberone with a GC purity of 96.6%.

Example 10

The apparatus is the same as in Example 9. 22.6 g of dibenzyl-o-carboxylic acid, 19.5 g of benzotrichloride and 1.0 g of $ZnCl_1$ (anhydrous) are heated at first to 80° C. When the production of HCl diminishes, the temperature is gradually increased to 150° C. The reaction ends after a total of 4½ h. Then the flask content is vacuum distilled. The fraction $bp_{0.2}$: 136°–40° C. consists of 15.3 g of dibenzosuberone having a GC purity of 95.1%.

Example 11

The apparatus is the same as in Example 9. 22.6 g of dibenzyl-o-carboxylic acid, 19.5 g of benzotrichloride and 50 mg of $FePO_4$ (anhydrous) are heated initially to 100° C. When the production of HCl diminishes the temperature is gradually raised to 150° C. The reaction ends after a total of 3 hours. The fraction $bp_{0.2}$: 136°–40° C. consists of 17.0 g of dibenzosuberone having a GC purity of 97.3%.

Example 12

The apparatus is the same as in Example 9. 22.6 g of dibenzyl-o-carboxylic acid, 13.9 g of 1-trichloromethyl-2-dichloromethylbenzene and 1.0 g of $FeCl_3$ (anhydrous) are heated initially at 100° C. When the production of HCl diminishes the temperature is gradually raised to 120° C. The reaction is ended after a total of 6¼ h. Then the flask contents are vacuum distilled. The fraction $bp_{0.2}$: 136°–40° C. consists of 12.4 g of dibenzosuberone having a GC purity of 95.8%.

Example 13

The apparatus is the same as in Example 9. 22.6 g of dibenzyl-o-carboxylic acid, 19.5 g of benzotrichloride, 1.0 g of $FeCl_3$ (anhydrous) and 70 ml of nitrobenzene are heated initially at 80° C. When HCl production diminishes the temperature is gradually raised to 110° C. The reaction ends after a total of 2 h. Then the flask contents are vacuum distilled. The fraction $bp_{0.2}$: 136°–40° C. consists of 20 g of dibenzosuberone with a GC purity of 92.2%.

Example 14

Exmple 9 is repeated with the equivalent amount of 2-[2-(m-methoxyphenyl)-ethyl]-benzoic acid (mp 117° to 119° C.) instead of dibenzyl-o-carboxylic acid, and the product, in a corresponding yield, is 2-methoxy-10,11-dihydro-5H-dibenzo[a,d]cycloheptene-5-one (mp 71° to 73° C. from a mixture of water and ethanol).

Examples 15 and 16

Example 9 is repeated with equivalent amounts of (a) 2-[2-p-methylphenyl)-ethyl]-benzoic acid (mp 82° C.) and (b) 2-[2-p-chlorophenyl)-ethyl]-benzoic acid (mp 122° C.), resulting in good yields of (a) 3-methyl-10,11-dihydro-5H-dibenzo[a,d]cycloheptene-5-one (mp 34° to 35° C.) and (b) 3-chloro-10,11-dihydro-5H-dibenzo[a,d-]cycloheptene-5-one (mp 64° to 65° C.).

It will be understood that the specification and examples are illustrative but not limitative of the present invention and that other embodiments within the spirit and scope of the invention will suggest themselves to those skilled in the art.

What is claimed is:

1. A process for preparing 10,11-dihydro-5H-dibenzo[a,d]-cyclopheptene-5-one compounds of the formula

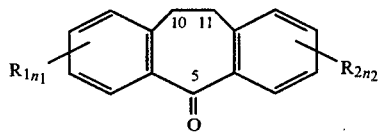

wherein one or more of the hydrogen can be replaced by one of $R_1$ and $R_2$, $R_1$ and $R_2$ being selected from halogen, alkyl, alkoxy, aryl, aralkyl, and carboalkoxy; and $n_1$ and $n_2$ are integers from 0–4; which process comprises cyclocondensation of the corresponding dibenzyl-o-carboxylic acid at temperatures from 50° C. to 180° C. in the presence of aromatic compounds containing one or more trichloromethyl groups on the aromatic ring and in the presence of a catalytic amount of 0.01 to 10 weight percent, based on corresponding dibenzyl-o carboxylic acid, of a Lewis acid.

2. The process as claimed in claim 1, wherein said Lewis acid is a zinc and/or iron compound.

3. The process as claimed in claim 1, wherein the catalyst is used in an amount of 0.02 to 5 weight percent.

4. The process as claimed in claim 1, wherein said aromatic compound is a mononuclear aromatic compound.

5. The process as claimed in claim 1, wherein said aromatic compound is used in a stoichiometric amount relative to said dibenzyl-o-carboxylic acid compound.

6. The process as claimed in claim 1, wherein the cyclocondensation is carried out at a temperature of 70° to 150° C.

7. The process as claimed in claim 6, wherein the cyclocondensation is carried out at a temperature of 75° to 150° C.

8. The process of claim 6 wherein the Lewis acid is a zinc and/or iron compound.

9. The process of claim 6 wherein the catalyst is used in amount of 0.02 to 5 weight percent.

10. The process of claim 6 wherein said aromatic compound is a mononuclear aromatic compound.

11. The process of claim 6 wherein said aromatic compound is used in a stoichiometric amount relative to said dibenzyl-o-carboxylic acid compound.

* * * * *